United States Patent [19]
Adler

[11] Patent Number: 5,573,495
[45] Date of Patent: Nov. 12, 1996

[54] ABDOMINAL WALL ELEVATOR DEVICE EMPLOYING ROTATABLE ARMS

[75] Inventor: David T. Adler, Manhasset, N.Y.

[73] Assignee: Flexbar Machine Corp., Central Islip, N.Y.

[21] Appl. No.: 293,076

[22] Filed: Aug. 19, 1994

[51] Int. Cl.[6] ................................................... A61B 17/02
[52] U.S. Cl. .......................... 600/204; 600/210; 600/214; 600/215; 600/219; 606/198
[58] Field of Search ............................ 600/204, 208–210, 600/714–716, 219, 225; 604/105, 108; 606/198; 411/344–46

[56] References Cited

U.S. PATENT DOCUMENTS

| | | | |
|---|---|---|---|
| 499,444 | 6/1893 | Schumann | 411/344 |
| 1,142,618 | 6/1915 | Pauley | 411/345 |
| 1,169,635 | 1/1916 | Grimes | 411/344 |
| 1,247,621 | 11/1917 | Bennett | 411/344 |
| 5,178,133 | 1/1993 | Pena | 128/20 |
| 5,232,443 | 8/1993 | Leach | 604/54 |
| 5,271,385 | 12/1993 | Bailey | 128/20 |

*Primary Examiner*—Richard J. Apley
*Assistant Examiner*—Kelly McGlashen
*Attorney, Agent, or Firm*—Charles I. Brodsky

[57] ABSTRACT

An abdominal wall elevator device including a pair of retractable tabs rotatable to 90° with respect to the vertical axis of the device, and selected of a dimension to enter the port of a Trocar in allowing low pressure pneumoperitoneum laparoscopic surgery. In a preferred embodiment of the invention, a removable push-rod incorporates a flat tip to operate on the tenons of a pair of hinges to swing the retractor tabs to the desired angle, to be locked in place.

11 Claims, 3 Drawing Sheets

ABDOMINAL WALL ELEVATOR DEVICE EMPLOYING ROTATABLE ARMS

FIELD OF THE INVENTION

This invention relates to laparoscopic surgery, in general, and to pneumoperitoneum laparoscopic surgery, in particular.

BACKGROUND OF THE INVENTION

Present techniques for laparoscopic surgery involve the establishment of pneumoperitoneum through carbon dioxide gas insufflation, which is necessary to provide a working cavity by displacing the peritoneum and anterior abdominal wall. As is understood, these techniques—utilizing a Trocar to puncture the abdominal wall, and a cannula to insufflate the carbon dioxide gas—offer several advantages over open surgery—for example, access to the abdominal cavity is achieved by only a small puncture incision yielding only small wounds, and a much shortened recovery period, measured in "days", rather than in "weeks". However, certain disadvantages have been noted.

For example: 1) maintenance of the exposure requires that there be airtight entry ports and a high flow insufflation—at inopportune moments, on the other hand, a loss of pneumoperitoneum may occur if there are leaks in the Trocar ports or during the insertion and/or use of the laparoscopic instrument; 2) the high pressure carbon dioxide insufflation oftentimes causes shoulder pain due to phrenic nerve irritation and may further threaten patients with pre-existing cardiopulmonary disease with gas embolism; 3) acid-based disturbances have also been noted with high flow carbon dioxide insufflation, which has been observed to lead to excessive patient cooling during lengthy procedures. Other studies, furthermore, suggest that these types of high-pressure procedures may not be desirable with obese patients, pregnant women, or for those suffering with chronic Bronchitis.

OBJECTS OF THE PRESENT INVENTION

It is an object of the present invention, therefore, to develop a laparoscopic surgical technique utilizing low pressure carbon dioxide gas insufflation.

It is another object of the invention to provide such a surgical technique in which half, or more, of the carbon dioxide gas can be jettisoned, or evacuated completely, after only a matter of a few minutes.

It is an additional object of the invention to provide such techniques while continuing to be able to lift the abdominal wall in allowing the surgical work to be performed in the abdominal cavity without injuring the inside of the stomach.

SUMMARY OF THE INVENTION

As will become clear from the following description, the present invention describes an abdominal wall elevator device as including a pair of retractable tabs or arms, rotatable to 90° with respect to the vertical axis of the device, and selected of a dimension to enter the port of the Trocar. In the preferred embodiment to be described, a removable push-rod incorporates a flat tip to operate on the tenons of a pair of hinges to swing the retractable tabs or arms to the desired angle to be locked in place. As will be described, this is accomplished by threading the push-rod to mate with internal threads of the cylindrical tube of the device where the push-rod is inserted—with all the component parts being dimensioned to afford a 12 mm round shape to pass through the Trocar opening. When fabricated of surgical grade stainless steel, with the retractable arms of 1¼" length, with the cylinder walls of 1.5 mm thickness and with the tenons hinged at 55°–60°, low pressure pneumoperitoneum laparoscopic surgery has been attainable as the retractable arms, with the invention, exhibit a lifting capacity of 30–40 pounds, in an empty abdominal cavity leaving enough room for the surgical repair or surgical procedure to be effectuated.

BRIEF DESCRIPTION OF THE DRAWING

These and other features of the present invention will be more clearly understood from a consideration of the following description, taken in connection with the accompanying drawing, in which:

FIG. 1 illustrates an enlarge view of the distal end of the device showing the arms in a closed position

DETAILED DESCRIPTION OF THE DRAWING

Figure 1:
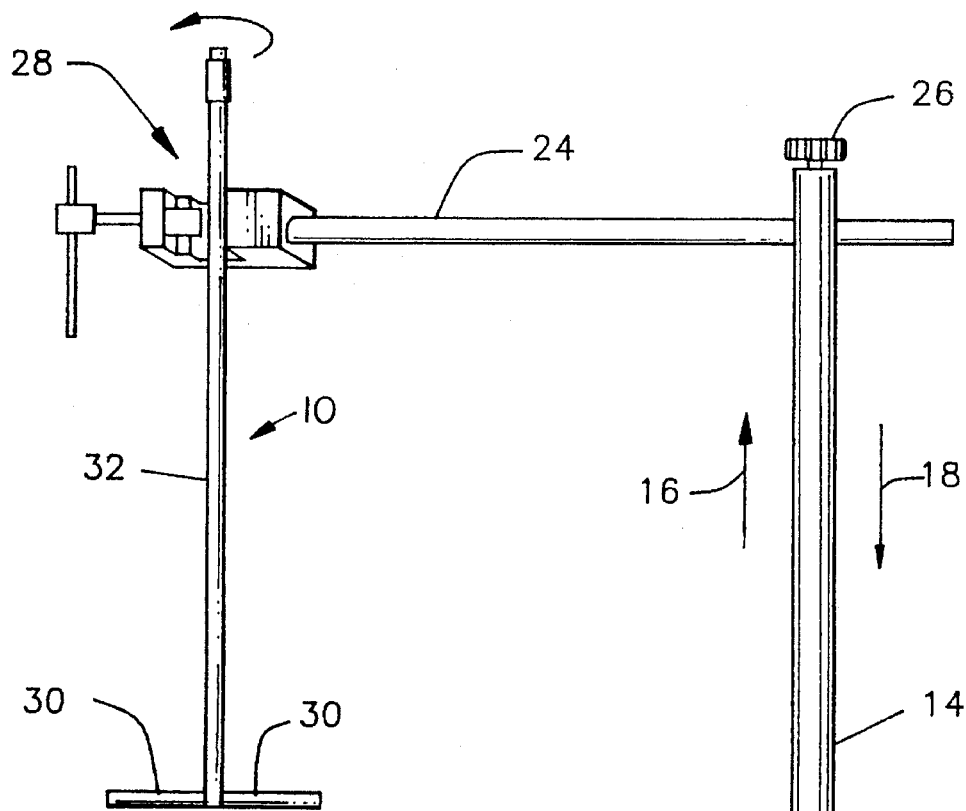
FIG. 1 illustrates a preferred manner of using the abdominal wall elevator device of the invention for low-pressure laparoscopic surgery.
Figure 1:
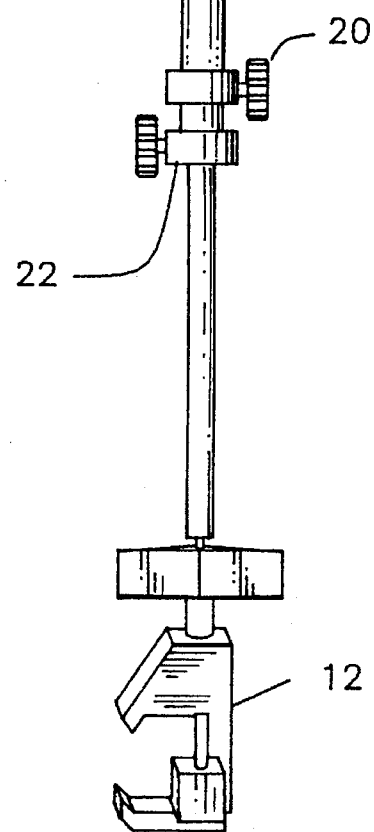
Figure 1A:
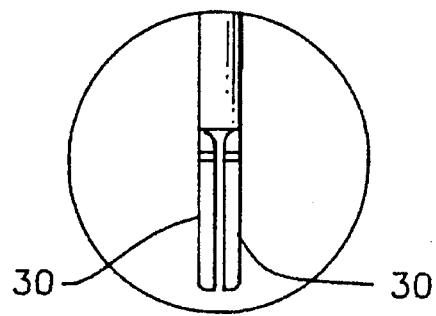

In FIG. 1, an adjustable support stand for the abdominal wall elevator 10 is shown as including a clamp 12 affixed to the operating room rail over a drape, and in connection with which a vertical distal tube 14 telescopes upwardly or downwardly, as at 16, 18 to reach the desired height. A proximal fluted thumb screw 20 and a proximal fluted security collar 22 are loosened and tightened, as required, in retracting the distal tube 14, or extending it, as desired. A horizontal bar 24 is shown, inserted through a hole adjacent the top of the distal tube 14, where it is secured by a further distal fluted thumb screw 26. A clamp 28 is shown at the opposite end of the horizontal bar 24 to receive the abdominal wall elevator, where it is clamped into the opened clamp and locked with slide lever screws, for example. Reference numeral 30 identifies the retractable tabs or arms of the elevator device as rotated to a Tee, or 90° position with respect to its vertical axis, while the insert at FIG. 1a shows the retractable arms closed. It will be understood that in the position shown in FIG. 1a, the arms 30 can then enter the port of a Trocar in order to make a puncture wound, with a connected cannula to insufflate the carbon dioxide gas mixture in known manner.

Figure 2A:
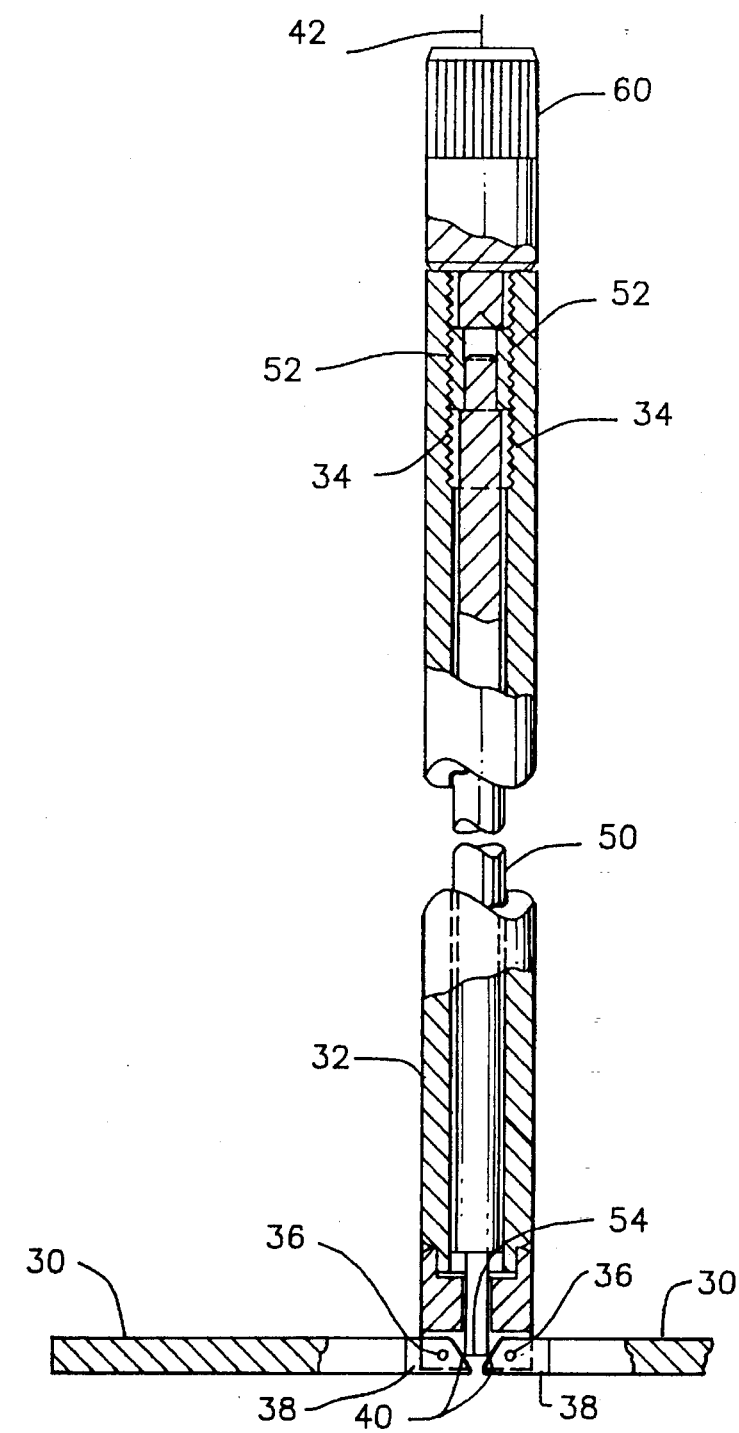
FIGS. 2a–2d illustrate sectional views of the abdominal wall elevator device helpful in an understanding of its operation.
Figure 2B:
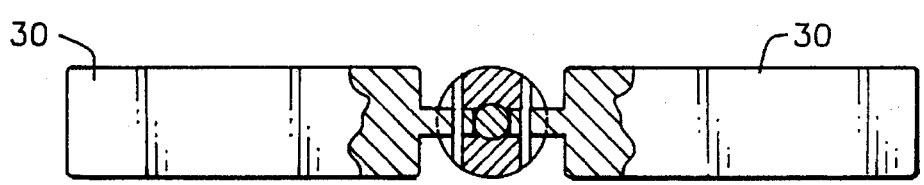
Figure 2C:
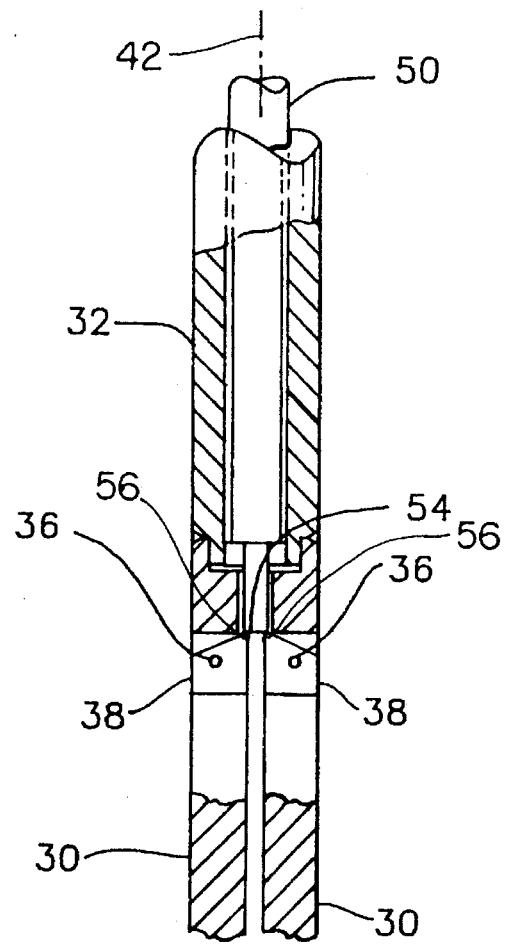

FIG. 2a and 2c illustrate partial front-sectional views of the components of abdominal wall elevator 10 with the arms 30 opened and closed, respectively. FIG. 2b, on the other hand, shows a partial bottom-sectional view of the abdominal wall elevator with the arms 30 opened. FIGS. 2a–2c illustrate the elevator 10 as incorporating a cylindrical tube 32—preferably of surgical grade stainless steel of 12 mm outer diameter and 1.5 mm wall thickness. Such cylindrical tube is internally threaded at one end, as at 34 and includes a pair of heat-treated pins 36 at its opposite end hinged to the retractable arms 30 by means of a pair of tenons 38. As indicated at 40, each of the tenons 38 are cut at an angle with respect to the central axis of the tube 32, shown at 42. Such cylindrical tube 32, pins 36 and hinges 38 are so designed that without any further disclosure, the retractable arms 30 would drop down by gravity to take the appearance shown in FIG. 2c.

The abdominal wall elevator of the invention, however, also includes a push-rod 50 threaded at one end 52 to match with, and mate, the internal threading of the cylinder 32, as at 34. Additionally, the push-rod 50 is provided at its other end with a flat tip 54 of a very slight radius, very critically aligned to bear against the tip edge 56 of the tenon 38, as more clearly shown in FIG. 2c. To effectuate the swinging of the retractor arms 30 from the FIG. 2c position, a knurled knob 60 is provided on the push-rod 50, rotatable both clockwise and counterclockwise.

In particular, rotating the knurled knob 60 in a clockwise direction threadingly moves the push-rod 50 along the tenons 38, causing the left-hand arm 30 of FIG. 2c to rotate clockwise, and the right-hand arm 30 of FIG. 2c to rotate counterclockwise. Continued turning of the knob 60 in the clockwise direction likewise continues the rotation of the arms 30, moving the push-rod along the slants 40 of the tenon 38, with the arms 30 then continuing their rotation about the pins 36. Further clockwise rotation of the knob 60 eventually swings the arms 30 to the 90° Tee position of FIG. 2a—and a slight additional rotation beyond 90° may be afforded by cutting a small recess in the outer wall of the cylindrical tube 32 (not shown) into which the retractable arm 30 may seat. FIG. 2b shows a bottom-sectional view of the fully opened abdominal wall elevator, to lift the abdominal wall with equal pressure from each hinge.

Figure 2D:
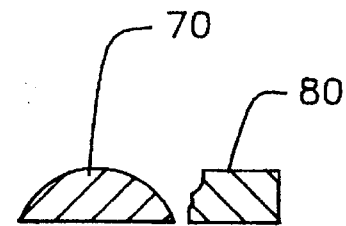

FIG. 2d shows an end view of the hinged arm 30, indicating it to be of convex, or semi-circular cross-section, and understood to be of a diameter substantially equal to that of the cylinder 32 (reference numeral 70). Reference numeral 80 of FIG. 2d illustrates the underside of the retractable arm 30 being generally flat. From the insert of FIG. 1a, with the retractable arms dropped to the closed position as shown in FIG. 2c, the flat surface areas of the arms 30 generally face one another.

As will be readily apparent, rotating the knurled knob 60 of the push-rod 50 in a counterclockwise direction serves to ease the pressure of the flat tip 54 against the slant 40 of the tenon 38, gradually allowing the retractable arm 30 to swing downward from its fully extended, 90° Tee position. Equally apparent is that the rotation of the knob 60 can be stopped at any time, effectively then locking the hinged arms 30 at any one of an infinite number of angles between the 0° position of FIG. 2c and the 90° position of FIG. 2a. This will be seen to allow the abdominal wall elevator device to be used with surgical patients of all size, whether it be a child, an adult, or an obese patient. As will be understood, the surgeon directs the angling through the knob rotation through observation of the procedure with a video linkage to a television monitor. In a preferred embodiment of the invention, the hinge and tenon areas and the tip of the push-rod are all heat treated to prevent "pitting" through continuing use, as might impair the security of the lock provided and the stability in operation.

As will be readily understood by those skilled in the art, with the elevator device of the invention inserted into the cavity insufflated with the carbon dioxide gas, the knurled knob 60 can then be brought into play in extending the retractable arms 30 to support the stomach and lift the abdominal walls. Once that is effected, the need for the high pressure gas is no longer required, so that it can be jettisoned in any amount desired via the cannula, or even evacuated entirely. As will also be appreciated, one unique safety feature of the invention follows in the event that one or both retractable arms might inadvertently catch onto some tissue or other viscera in the cavity—there, if that be the situation, the surgeon can entirely remove the push-rod 50 simply by rotating the knob 60 in a counterclockwise direction to retract the arm 30. Obviously, if simply a lowering of the arms frees the tissue, no need for the removal of the push-rod follows—but that latitude is affordable with the invention, where desired.

While there has thus been described what is considered to be a preferred embodiment of the present invention, it will be readily appreciated by those skilled in the art that modifications can be made without departing from the scope of the teachings herein, of utilizing an abdominal wall elevator to provide the working cavity yet without maintaining the constant pressure of a high flow carbon dioxide gas, and which can be easily disengaged, if necessary. For at least such reason, therefore, resort should be had to the claims appended hereto for a true understanding of the scope of the invention.

I claim:

1. An abdominal wall elevator device comprising:

a cylindrical tube having an internally threaded first end, an oppositely positioned second end, and a central axis;

a pair of retractor arms;

a pair of hinges respectively coupled to said pair of retractor arms for hinging each of said arms to said tube at said second end, with said hinges including a pair of tenons having oppositely slanted face surfaces of substantially equal angle;

a push-rod inserted within said tube at said first end, said push-rod terminating in a flat tip at a first end thereof and edges of said tip bearing against said slanted face surfaces of said pair of tenons;

wherein clockwise rotation of said push-rod results in said pair of retractor arms rotating to a position perpendicular to said central axis and wherein counterclockwise rotation of said push-rod results in said pair of retractor arms rotating to a position parallel to said central axis and extending distally from said tube;

wherein said push-rod is rotatable to open and close said pair of retractor arms in use as said tip edges bear against said slanted face surfaces;

and wherein said retractor arms are of a dimension to enter the port of a trocar used in laparoscopic surgery.

2. The abdominal wall elevator of claim 1, wherein said push-rod is controllably insertable within said tube to rotate said retractor arms from an angle substantially parallel with said central axis to an angle approximately 90° therewith or greater.

3. The abdominal wall elevator of claim 2, wherein said push-rod is externally threaded to mate with the internal threads of said cylindrical tube, in controlling rotation of said retractor arms to a predetermined angle with respect to the central axis of said tube according to the position of said pair of tip edges bearing against said slanted face surfaces of said pair of tenons.

4. The abdominal wall elevator of claim 3, wherein said push-rod also includes a knurled knob at a second end thereof.

5. The abdominal wall elevator of claim 3, wherein said push-rod is removably insertable within said tube at said first end.

6. The abdominal wall elevator of claim 5, wherein said pair of tenons and said flat tip of said push-rod are all heat-treated.

7. The abdominal wall elevator of claim 6, wherein said retractor arms are of convex cross-section.

8. The abdominal wall elevator of claim 7, wherein said pair of retractor arms are of a semi-circular cross-section.

9. The abdominal wall elevator of claim 8, wherein said pair of retractor arms are of a semi-circular cross-section of diameter substantially equal to that of said cylindrical tube.

10. The abdominal wall elevator of claim 9, wherein said cylindrical tube has an outer diameter of substantially 12 mm.

11. The abdominal wall elevator of claim 9, wherein said cylindrical tube is constructed of substantially 1.5 mm inner wall thickness.

* * * * *